US011661565B2

(12) United States Patent
Doszczak et al.

(10) Patent No.: US 11,661,565 B2
(45) Date of Patent: May 30, 2023

(54) ODOROUS ACETALS OF ETHYL VANILLIN AND ETHYL VANILLIN DERIVATIVES

(71) Applicant: S H KELKAR & COMPANY LIMITED, Mumbai (IN)

(72) Inventors: Leszek Doszczak, Amersfoort (NL); Andre Scholten, Berghem (NL); Wojciech I Dzik, Amsterdam (NL)

(73) Assignee: S H KELKAR & COMPANY LIMITED

( * ) Notice: Subject to any disclaimer, the term of this patent is extended or adjusted under 35 U.S.C. 154(b) by 242 days.

(21) Appl. No.: 15/733,266

(22) PCT Filed: Dec. 6, 2018

(86) PCT No.: PCT/EP2018/083753
§ 371 (c)(1),
(2) Date: Jun. 18, 2020

(87) PCT Pub. No.: WO2019/121032
PCT Pub. Date: Jun. 27, 2019

(65) Prior Publication Data
US 2020/0399560 A1  Dec. 24, 2020

(30) Foreign Application Priority Data

Dec. 20, 2017 (EP) ..................................... 17209062

(51) Int. Cl.
| | | |
|---|---|---|
| C11B 9/00 | (2006.01) | |
| A23L 27/20 | (2016.01) | |
| A23L 27/00 | (2016.01) | |
| A61K 8/34 | (2006.01) | |
| A61K 8/35 | (2006.01) | |
| A61K 8/49 | (2006.01) | |
| A61L 9/01 | (2006.01) | |
| A61Q 13/00 | (2006.01) | |
| C07C 41/54 | (2006.01) | |
| C07C 45/64 | (2006.01) | |
| C07D 317/22 | (2006.01) | |

(52) U.S. Cl.
CPC .......... *C11B 9/0061* (2013.01); *A23L 27/204* (2016.08); *A23L 27/84* (2016.08); *A61K 8/347* (2013.01); *A61K 8/35* (2013.01); *A61K 8/4973* (2013.01); *A61L 9/01* (2013.01); *A61Q 13/00* (2013.01); *C07C 41/54* (2013.01); *C07C 45/64* (2013.01); *C07D 317/22* (2013.01); *C11B 9/0076* (2013.01); *A23V 2002/00* (2013.01)

(58) Field of Classification Search
CPC .... C11B 9/0061; C11B 9/0076; A23L 27/204; A23L 27/84; A61K 8/347; A61K 8/35; A61K 8/4973; A61L 9/01; A61Q 13/00; C07C 41/05; C07C 45/64; C07D 317/22; A23V 2002/00
See application file for complete search history.

(56) References Cited

U.S. PATENT DOCUMENTS

| | | | |
|---|---|---|---|
| 3,636,158 A * | 1/1972 | Hinkley et al. | ....... C07C 255/00 |
| | | | 568/442 |
| 4,383,943 A | 5/1983 | Britten-Kelly et al. | |
| 4,473,588 A | 9/1984 | Wilson et al. | |
| 5,874,398 A | 2/1999 | Surburg et al. | |
| 2006/0034992 A1* | 2/2006 | Nelissen | ............... C07C 43/303 |
| | | | 426/534 |
| 2016/0333291 A1* | 11/2016 | Aida | ...................... A61Q 13/00 |
| 2019/0175777 A1* | 6/2019 | Iwai | ......................... C11B 9/00 |

FOREIGN PATENT DOCUMENTS

| | | | | |
|---|---|---|---|---|
| EP | 1705171 A1 | 9/2006 | | |
| JP | S57188537 A | 11/1982 | | |
| JP | 2017210589 A | * 11/2017 | ............... | A61L 9/01 |
| WO | 9734578 A1 | 9/1997 | | |
| WO | 2011132098 | 10/2011 | | |

OTHER PUBLICATIONS

International Search Report and Written Opinion dated Jan. 4, 2019, in related PCT Application No. PCT/EP2018/083753.
John Ralph et al, "Identification and Synthesis of New Ferulic Acid Dehydrodimers Present in Grass Cell Walls", Jan. 1, 1994 (Jan. 1, 1994), p. 3485, Retrieved from the Internet: URL:http://pubs.rsc.org/en/content/articlepdf/1994/p1/p19940003485 XP055227539 Scheme 3;p. 3490; compounds 22, 23.

\* cited by examiner

*Primary Examiner* — Michael P Cohen
(74) *Attorney, Agent, or Firm* — Maschoff Brennan

(57) ABSTRACT

The present invention relates to new odorous acetals which are useful as fragrance or flavor materials in particular in providing vanilla and spicy notes with a natural impression resembling vanilla absolute.

17 Claims, No Drawings

ODOROUS ACETALS OF ETHYL VANILLIN AND ETHYL VANILLIN DERIVATIVES

FIELD OF THE INVENTION

The present invention relates to new odorous acetals which are useful as fragrance or flavor materials in particular in providing vanilla and spicy notes with a natural impression resembling vanilla absolute.

BACKGROUND OF THE INVENTION

Substituted 2-alkoxyphenols have a broad range of applications in foodstuffs and in perfumery compositions. For example vanillin, ethyl vanillin, methyl diantillis, eugenol, or Ultravanil are used to achieve sweet, spicy and smoky notes in perfumery and flavor compositions. In particular, there is a demand for novel balsamic and vanilla notes that have superior performance and are more air-stable than e.g. vanillin; for example, WO2011132098 discloses alkyl aryl carbonates as perfuming ingredients to impart spicy and/or balsamic notes, in particular of the vanilla type.

Generally, the use of 2-alkoxyphenols in perfumery has certain limitations due to their rather low performance in alkali media (e.g. soaps, shampoos, washing powders) as their tendency to discolor in air and in certain products which is an intrinsic property of phenols. These limitations can be overcome by functionalization of the phenolic OH group which prevents the formation of non-volatile phenoxyl anions and retards the oxidation of the aromatic ring. However, for the majority of vanilla compounds with a protected hydroxyl group the odor intensity decreases and the odor notes may differ from the parent compound. Also the odorous nature of the protecting group can cause presence of unpleasant off-notes in aged products. For instance, ethyl vanillin acetate or vanillin isobutyrate can generate rancid/acidic off-notes upon hydrolysis. Notably, there is a limited number of odorants with vanilla odor as small changes to the vanillin structure cause substantial change to the odor. For instance, isovanillin smells much weaker (nearly odorless) and mainly herbaceous. Thus, the development of new molecules that feature a vanilla odor yet are stable in perfumery bases remains a challenge. Below are the most important commercially available compounds that feature a vanilla odor:

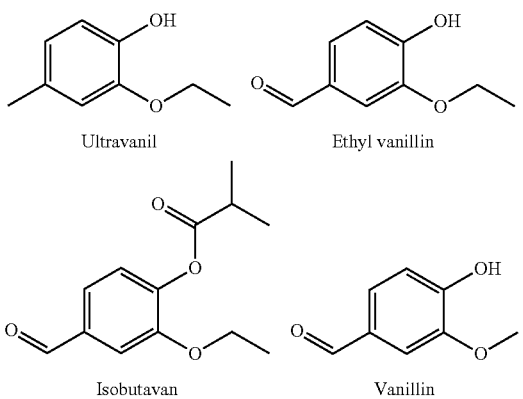

Ultravanil

Ethyl vanillin

Isobutavan

Vanillin

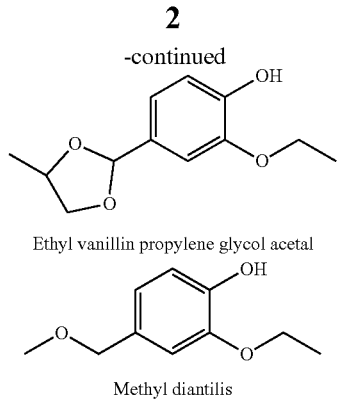

Ethyl vanillin propylene glycol acetal

Methyl diantilis

Ultravanil: Vanilla, Sweet, Phenolic
Ethyl vanillin: Sweet, Creamy, Vanilla, Caramellic
Isobutavan: Vanilla, Sweet, Fruity
Vanillin: Sweet, Vanilla, Creamy, Chocolate
Ethyl vanillin propylene glycol acetal: Sweet, Vanilla, Creamy, Spicy
Methyl diantillis: Spicy, Carnation, Sweet, Vanilla The hydroxyl group of 2-alkoxyphenols was disclosed to form esters with carboxylic acids (e.g. isobutavan, U.S. Pat. No. 4,473,588) or alkylcarbonate esters (WO2011132098). Formation of such esters is however accompanied with generation of significant amount of waste. Since the reduction of waste formed during chemical processes is crucial from both environmental and economical points of view, we searched for alternative methods for the functionalizaton of the phenolic group. These methods should allow for the generation of novel fragrant materials with vanilla notes and have an additional advantage of reducing the amount of, or more preferably eliminating waste. Therefore, we turned our attention to the use of acetaldehyde ethyl acetal as a protecting group of the hydroxyl moiety, which can be introduced with 100% atom economy by reacting phenols with ethoxyethene using Brønsted acid as a catalyst. The acetal of vanillin was prepared as a synthetic intermediate (U.S. Pat. No. 3,636,158A) for pharmaceutical products (antihypertensive agent), however, no olfactory properties were disclosed for this molecule. Notably, to date, no acetaldehyde ethyl acetals giving vanilla-like fragrance were reported.

SUMMARY OF THE INVENTION

This invention discloses novel compounds of formula (1), formula (2), formula 0 of formula (4) and their use in fragrance, flavor and/or deodorizing/masking compositions.

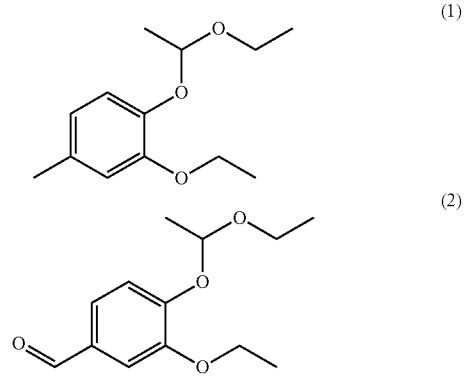

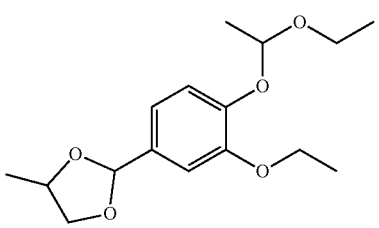

(3)

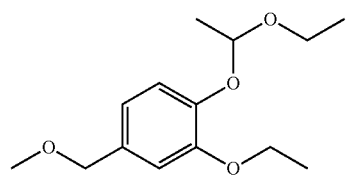

(4)

The new acetals disclosed below have a clear vanilla-like character and compared to their parent phenols have greater substantivity and persistence. They retain the odor of the parent phenol to high extent while slightly modifying the odor profile. Additionally, the new acetals have an increased air- and photo-stability in media such as candle wax and soap.

DETAILED DESCRIPTION

The term "odorant" characterizing the compounds according to the present invention means that in humans it triggers an odor sensation which is preferably pleasant; it is therefore conventionally used for perfuming industrial and sanitary articles, washing agents, cleaning agents, personal hygiene products, cosmetics and the like. For the purposes of the present invention and appended claims, the term "odorant" includes "aroma substances". Aroma substances is the term usually used to designate substances which provide odor and/or flavor to foodstuffs.

The acetal compounds of formula (1), formula (2), formula (3) or of formula (4) be used alone, as mixtures thereof, or in combination with a base material.

As used herein, the "base material" includes all known fragrance/flavor materials selected from the extensive range of natural products like: essential oils, extracts, resinoids or isolates and synthetic materials currently available, such as: hydrocarbons, alcohols, aldehydes and ketones, ethers and acetals, esters and lactones, nitriles, oximes or heterocycles, and/or in admixture with one or more ingredients or excipients/adjuvants conventionally used in conjunction with odorants in fragrance and/or flavor compositions, for example: solvents/diluents, stabilizers, carrier materials, and other auxiliary agents commonly used in the art.

The acetal compounds of formula (1), formula (2), formula (3) or of formula (4) may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients.

According to a preferred embodiment of the invention, the fragrance, flavor and/or deodorizing/masking composition according to the present invention contains at least one acetal compound according to formula (1), formula (2), formula (3) or of formula (4) as previously described, in quantities between 0.0001 and 95 wt. %, for example between 0.001 and 25 wt. %, preferably between 0.01 and 15 wt. %, more advantageously between 0.1 and 10 wt. %, in particular between 1 and 5 wt. %, in each case relative to the entire composition.

According to a particularly preferred embodiment of the invention, in addition to the compound of formula (1), formula (2), formula (3) or of formula (4) according to the present invention, the fragrance, flavor and/or deodorizing/masking composition according to the present invention contains additional odorants, for example in a quantity of 0.1 to 99.9 wt. %, preferably 5-90 wt. %, in particular 15-70 wt. %, relative to the entire fragrance and/or flavor composition.

The compounds of formula (1), formula (2), formula (3) or of formula (4) as described above may be employed in a consumer product base simply by directly mixing at least one compound of formula (1), formula (2), formula (3) or of formula (4) with the consumer product base; or they may, in an earlier step, be entrapped with an entrapment material, for example, polymers, capsules, microcapsules and/or nanocapsules, liposomes, film formers, absorbents such as active carbon or zeolites, cyclic oligosaccharides, cyclic glycourils, and mixtures of two or more thereof, or they may be chemically bonded to substrates, which are adapted to release the fragrance molecule upon application of an external stimulus such as light, enzyme, air, water or the like, and then mixed with the consumer product base.

Thus, the invention can be useful for existing methods of manufacturing a fragrance, flavor and/or deodorizing/masking composition, comprising the incorporation of a compound of formula (1), formula (2), formula (3) or of formula (4) as a fragrance, flavor and/or deodorizing/making ingredient, either by directly admixing the compound to the consumer product base or by admixing a fragrance, flavor and/or deodorizing/masking composition comprising said compound of formula (1), formula (2), formula (3) or of formula (4), which may then be mixed with a consumer product base, using conventional techniques and methods. Through the addition of an olfactory-acceptable amount of at least one compound of formula (1), formula (2), formula (3) or of formula (4) of the present invention as described, the odor notes of a consumer product base can be improved, enhanced, and/or modified.

The present invention provides fragrance, flavor and/or deodorizing/masking compositions comprising an acetal selected from compounds of formula (1), formula (2), formula (3) or of formula (4).

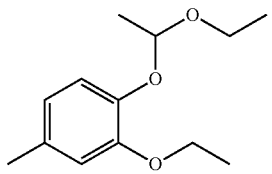

(1)

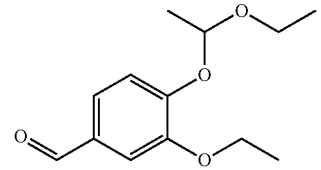

(2)

-continued

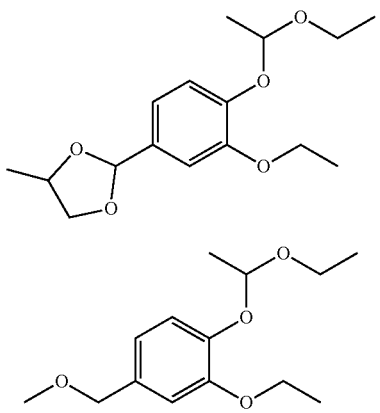

Where compound (1) is 2-ethoxy-1-(1-ethoxyethoxy)-4-methylbenzene; compound (2) is 3-ethoxy-4-(1-ethoxyethoxy)benzaldehyde; compound (3) is 2-(3-ethoxy-4-(1-ethoxyethoxy)phenyl)-4-methyl-1,3-dioxolane; compound (4) is 2-ethoxy-1-(1-ethoxyethoxy)-4-(methoxymethyl)benzene.

The Applicants have also discovered that, from an olfactory perspective, the compounds of formula (1), formula (2), formula (3), or of formula (4) have distinctly vanilla and spicy notes with suprisingly natural impression resembling vanilla absolute or pimento berry oil. Furthermore, compared their parent phenol odorants e.g. 2-ethoxy-4-methylphenol (ultravanil) for compound of formula (1), 3-ethoxy-4-hydroxybenzaldehyde (ethyl vanillin) for compound of formula (2), 2-ethoxy-4-(4-methyl-1,3-dioxolan-2-yl)phenol (ethyl vanillin propylene glycol acetal) for compound of formula (3) and 2-ethoxy-4-(methoxymethyl)phenol (methyl diantilis) for compound of formula (4), the compounds of formula (1), formula (2) formula (3) and formula (4) have greater substantivity and persistence. They retain the odor of the parent phenol to high extent, while slightly modifying the odor profile. The changes in the odor profile compared to the parent phenol compound are listed in the table below

| Compound structure | Odor profile |
|---|---|
| 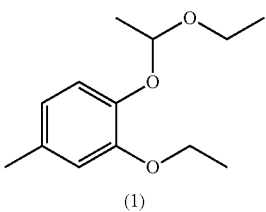 [SMILES: CCOc1cc(C)ccc1OC(C)OCC] (1) | Less phenolic, more vanillic; with an aspect of vanilla absolute |
| 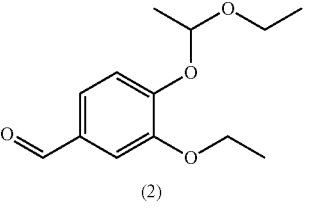 [SMILES: CCOc1cc(C=O)ccc1OC(C)OCC] (2) | Natural, more vanillic, caramel |
| 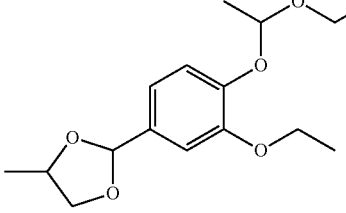 (3) | More chocolate note, nice spicy, clove |
| 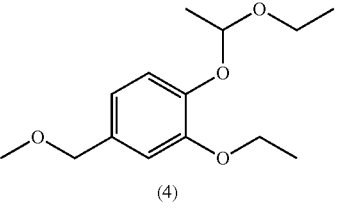 [SMILES: CCOc1cc(COC)ccc1OC(C)OCC] (4) | More sweet |

The Applicants have also discovered that, the acetals have a generally improved color stability in soap, candle wax and other media (e.g. 3-methoxy-3-methyl-1-butanol used as a base for incense). For instance when compound of formula (1) is used in a candle wax base (e.g. at 0.3 wt % concentration), no discoloration of the material was observed after standing in a sunlit location at room temperature for four weeks whereas when the parent phenol, 2-ethoxy-4-methylphenol, was used at the same molar concentration, the yellowing of the candle wax could be easily observed. Similarly, under the same conditions, the discoloration of a soap base comprising compound of formula (2) and/or compound of formula (3) (e.g. a soap base comprising 1 wt % of compound (2) or a soap base comprising 1 wt % of compound (3)) or of an incense base comprising compound of formula (2) and/or compound of formula (3) (e.g. an incense base comprising 4 wt % of compound (2) or an incense base comprising 4 wt % of compound (3)) was significantly slower compared the control samples comprising the respective parent phenols ethyl vanillin and 2-ethoxy-4-(4-methyl-1,3-dioxolan-2-yl)phenol (ethyl vanillin propylene glycol acetal).

In an embodiment of the present invention, the claimed fragrance, flavor and/or deodorizing/masking composition is advantageously used as a perfumery composition. Perfumery compositions according to the present invention generally include a perfume, a cologne, an eau du toilette, and/or an eau de parfum. In an embodiment of the present invention, the claimed fragrance, flavor and/or deodorizing/masking composition is advantageously used in a cosmetic formulation, a personal care product, a cleansing product, a fabric softener, and/or air freshener, and the like. Furthermore, it is within the purview of embodiments of the invention that the novel fragrance, flavor and/or deodorizing/masking composition(s) and/or novel compound(s) of formula (1), formula (2), formula (3) or of formula (4) described herein may be integrated into building materials, wall and floor coverings, vehicle components, and the like.

In an embodiment, the present invention also provides new compounds of formula (1), formula (2), formula (3) or of formula (4) useful in the perfume, aroma and/or deodorizing/masking compositions of the present invention.

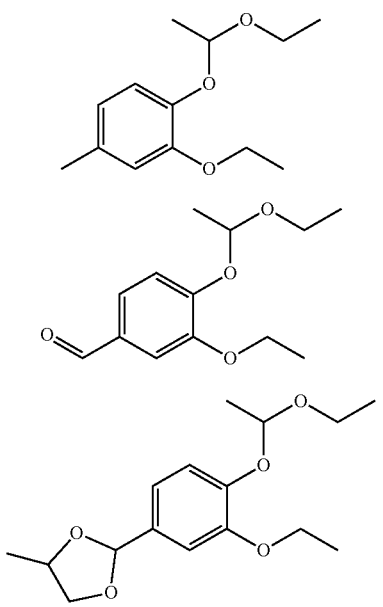

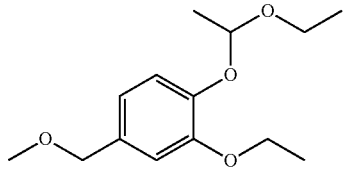

Where compound (1) is 2-ethoxy-1-(1-ethoxyethoxy)-4-methylbenzene; compound (2) is 3-ethoxy-4-(1-ethoxyethoxy)benzaldehyde; compound (3) is 2-(3-ethoxy-4-(1-ethoxyethoxy)phenyl)-4-methyl-1,3-dioxolane; compound 4) is 2-ethoxy-1-(1-ethoxyethoxy)-4-(methoxymethyl)benzene.

In an embodiment, the compounds of formula (1), (2), (3) and (4) can advantageously be prepared from compounds of formula (5), (6), (7), (8) respectively

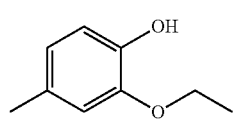

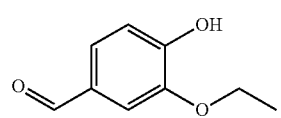

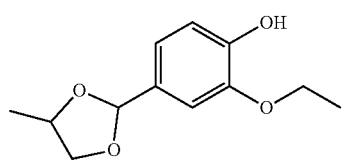

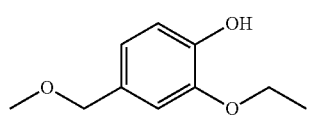

by using an acetalization synthesis step. Any appropriate acetalization process leading to compound of formula (1), (2), (3) and (4) can be used; as illustrative and non-restricting example, the acetalization is performed e. g. by reacting the said compounds of formula (5), (6), (7), (8) with ethoxyethene in the presence of catalytic amounts of an acid (e.g hydrochloric acid, sulphuric acid, phosphoric acid, etc.) in the presence of a suitable solvent (e.g. dichloromethane, ethyl acetate etc.), or without solvent in which case ethoxyethene plays a role of a solvent and a reactant. In an embodiment of the present invention, the synthesis of acetals (1), (2), (3) and (4) can be thus realized according to the following approach:

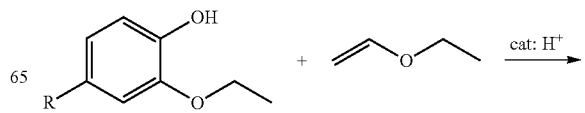

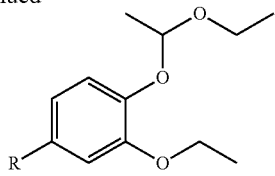

In general, in addition to the novel odorant and/or fragrance, flavor and/or deodorizing/masking compositions described herein, suitable fragrance, flavor or deodorizing compositions may advantageously include conventional ingredients such as, for example, solvents carriers, stabilizers, emulsifiers, moisturizers, dispersants, diluents, thickeners, thinners, other odorants, and/or adjuvants, and the like.

The compounds of formula (1), formula (2), formula (3) or of formula (4) co with numerous known natural or synthetic fragrance, flavor and/or deodorizing/masking materials, whereby the range of the natural ingredients can embrace not only readily-volatile but also semi-volatile and slightly-volatile components and the range of the synthetic ingredients can embrace representatives from many classes of substances, as will be evident from the following non-limitting compilation:

Natural products such as:

Ajowan oil, Amyris oil, Armoise oil, A emisia oil, Basil oil, Bees wax absolute Bergamot oil, Birch tar oil, Black pepper oil, Black pepper oleoresin, Camphor oil Cananga oil, Caraway oil, Cardamom oil, Carrot seed oil, Castoreum absolute, Cedar leaf oil, Cedarwood oil, Celery seed oil, Chamomile oil, Cinnamon bark oil, Cinnamon leaf oil, Cistus absolute, Cistus oil, Citronella oil, Citronella terpenes, Clary sage oil, Clove oil rectified, Cognac oil white, Coriander seed oil, Cumin seed oil, Cypress oil, Davana oil, Dill seed oil, Elemi oil, Elemi resinoid, Eucalyptus oil, Fir needle oil, *Galbanum* oil, Geranium oil, Ginger oil Indian, Grapefruit oil, Guaiacwood oil, Gurjun balsam, Jasmin absolute, Jatamansi oil, Juniper berry oil, Juniper leaf oil, Kachur oil, Labdanum absolute, Labdanum resinoid, Lavender oil, Lemon oil, Lemon oil terpenes, Lemongrass oil, Lime oil, *Litsea cubeba* oil, *Litsea cubeba* terpenes, Lobhan choya resinoid, Mandarin oil, Mentha arvenis oil, *Mentha citrata* oil, *Mimosa* absolute, Myrrh resinoid, Nagarmotha oil, Nutmeg oil, Oakmoss absolute, Oakmoss resinoid, Olibanum oil, Olibanum resinoid, Orange oil, *Origanum* oil, Palma rosa oil, Patchouli oil, Peppermint oil, Peru Balsam resinoid, Petitgrain oil, Pine needle oil, Pink pepper oil, Rose absolut, Rose oil, Rosemary oil, Sandalwood oil, Seaweed absolute, Spearmint oil, Sugandh kokila oil, Sugandh mantri oil, Tagete oil Tolu Balsam resinoid, Tuberose absolute, Turmeric oil, Turpentine oil, Valerian oil, Vetiver oil, Vetiver terpenes.

Synthetic raw materials for instance:

Esters such as: Aldehyde C16, Allyl amyl glycolate, Allyl caproate, Allyl cyclohexyl propionate, Allyl heptoate, Allyl phenoxy acetate, Amyl acetate iso, Amyl benzoate, Amyl butyrate, Amyl caproate, Amyl cinnamate, Amyl isovalerate, Amyl phenyl acetate, Amyl propionate, Amyl salicylate iso, Amyris acetate, Anisyl acetate, Benzyl acetate, Benzyl benzoate, Benzyl butyrate, Benzyl cinnamate, Benzyl formate, Benzyl isobutyrate, Benzyl isoeugenol, Benzyl propionate, Benzyl salicylate, Benzyl tiglate, Butyl acetate, Butyl butyrate Butyl butyryl lactate, Caryophyllene acetate, Cedryl acetate, Cinnamyl acetate, Cinnamyl butyrate, Cis-3-hexenyl acetate, Cis-3-hexenyl benzoate, Cis-3-hexenyl caproate, Cis-3-hexenyl formate, Cis-3-hexenyl isobutyrate, Cis-3-hexenyl-2-methyl butyrate, Cis-3-hexenyl propionate, Cis-3-hexenyl salicylate, Cis-3-hexenyl tiglate, Citronellyl acetate, Citronellyl butyrate, Citronellyl formate, Citronellyl isobutyrate, Citronellyl propionate, Citronellyl tiglate, Cyclabute, Cyclogalbanate, Cyclohexyl ethyl acetate, Decyl acetate, Dibutyl phthalate, Diethyl malonate, Diethyl phthalate, Dihydromyrcenyl acetate, Dimethyl octanyl acetate, Dimethyl phenyl ethyl carbinyl acetate, Dioctyl adipate, Dioctyl phthalate, Dimethyl benzyl carbinyl acetate, Dimethyl benzyl carbinyl butyrate, Ethyl linalyl acetate, Ethyl 2-methyl butyrate, Ethyl 3-phenyl propionate, Ethyl acetate, Ethyl acetoacetate, Ethyl benzoate, Ethyl butyrate, Ethyl caprate C10, Ethyl caproate C6, Ethyl caprylate C8 Ethyl cinnamate, Ethyl heptoate, Ethyl hexyl acetate, Ethyl isobutyrate, Ethyl laurate, Ethyl pelargonate, Ethyl phenoxy acetate, Ethyl phenyl acetate, Ethyl phenyl glycidate, Ethyl propionate, Ethyl safranate, Ethyl salicylate, Ethyl valerate, Eugenyl acetate, Evernyl, Fenchyl acetate, Floramat, Frescolat ML, Fructone, Fruitate, Geranyl acetate, Geranyl butyrate, Geranyl formate, Geranyl propionate, Geranyl tiglate, Givescone, Guaiol acetate, Hedionate, Hedione, Helvetolide, Herbanate, Hexyl acetate, Hexyl benzoate, Hexyl butyrate Hexyl caproate, Hexyl isobutyrate, Hexyl propionate, Hexyl salicylate, Isobomyl acetate Isobutyl acetate, Isobutyl phenyl acetate, Isobutyl salicylate, Isoeugenyl acetate, Isononyl acetate, Isopentyrate, Isopropyl 2-methyl butyrate, Isopropyl myristate, Jasmonyl, Liffarome, Linalyl acetate, Mahagonate, Manzanate, Menthanyl acetate, Menthyl acetate, Methyl benzoate, 2-Methyl butyl acetate, Methyl camomille, Methyl cinnamate, Methyl cyclogeranate, Methyl heptine carbonate, Methyl laurate, Methyl octine carbonate, Methyl phenyl acetate, Methyl salicylate, Methyl-2-methyl butyrate, Neofolione, Nopyl acetate, Octenyl acetate, Octyl acetate, Octyl isobutyrate, Para cresyl acetate, Para cresyl isobutyrate, Para cresyl phenyl acetate, Pear ester, Peranat, Phenoxy ethyl isobutyrate, Phenyl ethyl acetate, Phenyl ethyl butyrate, Phenyl ethyl formate, Phenyl ethyl isobutyrate, Phenyl ethyl phenyl acetate, Phenyl ethyl propionate, Phenyl ethyl salicylate, Phenyl ethyl tiglate, Phenyl propyl isobutyrate, Prenyl acetate, Romandolide, Sagecete, Styrallyl acetate, Styrallyl propionate, Tangerinol, Terpinyl acetate, Thesaron, trans-2-Hexenyl acetate, Tropicate, Verdox, Verdyl acetate, Verdyl propionate, Vertenex, Vetikol acetate, Vetiveryl acetate, Yasmolys.

Lactones such as: Ambrettolide, Arova N, Celeriax, Decalactone delta, Decalactone gamma, Dodecalactone delta, Dodecalactone gamma, Ethylene brassylate, Exaltolide, Heptalactone gamma, Hexalactone delta, Hexalactone gamma, Methyl laitone, Methyl octalactone, Nonalactone delta, Nonalactone gamma, Octahydrocoumarine, Octalactone delta, Octalactone gamma, Rootylone, Silvanone supra, Undecalactone delta, Undecalactone gamma, Valerolactone gamma, 10-Oxa HexaDecanolide (OHD musk), Coumarin, Habanolide, Jasmolactone.

Aldehydes such as: Acetaldehyde, Adoxal, Aldehyde C10, Aldehyde C11 iso, Aldehyde C11 moa, Aldehyde C11 undecylenic, Aldehyde C11 undecylic, Aldehyde C12 lauric, Aldehyde C12 MNA, Anisaldehyde, Amyl cinnamaldehyde, Benzaldehyde, Bourgeonal, Campholenaldehyde, Cantonal, Cetonal, Cinnamic aldehyde, Cis-4-decenal, Cis-6-nonenal, Citral, Citronellal, Citronellyl oxyacetaldehyde, Cocal, Cuminaldehyde, Curgix, Cyclal C, Cyclamen aldehyde, Cyclomyral, Cyclovertal, Decenal-9, Dupical, Empetal, Ethyl vanillin, Floralozone, Florhydral, Geraldehyde, Helional, Heliotropin, Heptanal, Hexanal, Hexyl cinnamaldehyde, Hivemal neo, Hydratropaldehyde, Hydroxycitronellal, Intreleven aldehyde, Isobutavan, Isocyclocitral, Isovaleraldehyde, Lilial, Limonenal, Maceal, Mefranal, Melonal Methyl cinnamaldehyde, trans,cis-2,6-Nonadienal, Nonanal, Octanal, Oncidal, Para tolyl aldehyde, Phenyl acetaldehyde, Phenyl propyl aldehyde, Precyclemone B, Safranal, Salicylaldehyde, Scentenal, Syringa aldehyde, trans-4-Decenal, trans-2-Dodecenal, trans-2-Hexenal, trans-2-Nonenal, Trifernal, Vanillin, Veratraldehyde, Vemaldehyde Ketones such as: Acetanisol, Acetoin, Acetophenone, Aldron, Benzophenone, Benzyl acetone, Calone, Camphor, Carvone d-, Carvone l-, Cashmeran, Cedryl methyl ketone, Cepionate, Claritone, Cosmone Crysolide, Cyclotene, Damascenone, Damascone alpha, Damascone beta, Damascone delta, Damascone gamma, Diacetyl, Dihydro beta ionone, Dihydro isojasmonate, Dimethyl octenone, Dynascone, Ethyl amyl ketone, Ethyl maltol, Fenchone, Filbertone, Geranyl acetone, Globanone, Heptyl cyclopentanone, Hexyl cyclopentanone, Ionone alpha, Ionone beta, Ionone pure, Iriswood, Irone alpha, Iso E Super, Isofenchone, Isojasmone T, Isolone K, Isomenthone, Isophorone, Jasmone cis-, Kambernoir, Kephalis, Koavone, Lavendinal, Maltol, Menthone, Methyl acetophenone, Methyl amyl ketone, Methyl heptenone, Methyl hexyl ketone, Methyl ionone gamma, Methyl naphthyl ketone beta, Methyl nonyl ketone, Muscenone, Muscone, Nectaryl, Orinox, OTBC Ketone, Para tertbutylcyclohexanone, Patchwood, Phantolid, Pharaone, Piperitone, Plicatone, Raspberry ketone, Raspberry ketone methyl ether, Safraleine, Spirogalbanone pure, Tonalid, Trimofix O, Veloutone, Vetikon.

Alcoholos such as: Alcohol oxo C13, Amber core, Ambermax, Ambrinol, Amyl vinyl carbinol, Anisic alcohol, Bacdanol, Benzyl alcohol, Butanol, Cedrol crystals, Cinnamic alcohol, Citronellol, Coranol, Decanol, Dimethyl benzyl carbinol, Dimethyl octanol, Dimethyl phenyl ethyl carbinol, Dimetol, Fenchol, Hexanol, Isoborneol, Isobornyl cyclohexanol, Javanol, Keflorol, Kohinool, Lauryl alcohol, Lilyflore, Linalool oxide, Mayol, Menthol, Norlimbanol, Octanol, Osyrol, Para tertbutylcyclohexanol, Phenoxanol, Phenoxyethanol, Phenyl ethyl alcohol, Phenyl propyl alcohol, Propylene glycol, Rosaphen, Rose glycol, Styrallyl alcohol, Tricyclodecane dimethanol, Tetrahydro linalool, Tetrahydro myrcenol, Timberol, Undecavertol, Cis-3-hexenol, Citronellol laevo, Cyclofloranol, Dihydrolinalool, Dihydromyrcenol, Dimyrcetol, Ebanol, Geraniol, Isopulegol, Linalool, Nerol, Nerolidol, trans,cis-2,6-Nonadienol, Polysantol, Rosalva, Sandalmysore core, Sandalore, Terpinen-4-ol, Terpineol, trans-2-Hexenol Phenols such as: Butylated hydroxyanisole, Dihydroeugenol, Eugenol pure, Guaiacol, Isoeugenol, Meta cresol, Methyl diantilis, Para cresol, Propenyl guaethol, Thymol, Ultravanil.

Ethers such as: Ambroxan, Anethole, Anther, Benzyl isoamyl ether, Benzyl isopropyl ether, Benzyl isovalerate, Boisiris, Cedramber, Cetalox, Decyl methyl ether, Dibenzyl ether, Dihydro rose oxide, Dimethyl hydroquinone, Dimethyl resorcinol, Diphenyl oxide, Doremox, Estragole, Ethyl linalool, Eucalyptol, Galaxolide, Gyrane, Herbavert, Lime oxide, Madrox, Methyl isoeugenol, Naphthyl isobutyl ether beta, Nerol oxide, Nerolin bromelia, Para cresyl butyl ether, Para cresyl methyl ether, Petiole, Phenyl ethyl methyl ether, Rhubafuran, Rose oxide, Rosyrane, Trisamber, Vetylbois K, Yara yara Acetals such as: Acetal CD, Acetal R, Amberketal, Boisambrene forte, Citrathal, 1,1-Diethoxyethane, Emeraldine, Freshopa, Herboxane, Indoflor, Jacinthaflor, Ma Spirambrene, Viridine, Elintaal, Glycolierral, Karanal, Methyl pamplemousse, Hydrocarbons such as: Bisabolene, Camphene, Carene delta 3, Caryophyllene, Cedrene, Cymene para, Dipentene, Diphenyl methane, Isolongifolene, Limonene d-, Longifolene, Myrcene, Naphthalene, Ocimene, Phellandrene alpha, Pinene alpha, Pinene beta, Styrene, Terpinene gamma, Terpinolene, 1,3,5-Undecatriene, Verdoracine.

Sulphur compounds such as: Corps cassis, Dibutyl sulphide, Dimethyl sulphide, Exovert, Grapefruit thiol, Oxane, Ribes mercaptan, Sulfurol, Thiocineol. Nitriles such as: Cinnamyl nitrile, Citronellyl nitrile, Citronitrile, Clonal Cumin nitrile, Irisnitrile, Lemonile, Peonile, Tridecyl nitrile, Agrumen nitrile, Decyl nitrile. Oximes such as: Buccoxime, Labienoxime, Stemone.

Nitrogen heterocycles such as: 2-acetylpyrazine, 2-acetylpyridine, sec-butylquinoline, Corps racine, 2-Ethyl-3,5(or 6)-dimethylpyrazine, Furfuryl pyrrole, Indole, Isobutyl quinoline, 2-Isobutyl-3(or 6)-methoxypyrazine, Isopropyl quinoline, *Maritima, p*-Methyl quinoline, Skatol, 2,3,5-Trimethylpyrazine.

Nitro compound such as: Musk Ketone

Schiff bases such as: Aurantiol, Helianthral, Ligantraa, Verdantiol.

Other materials such as: Acetanilide, Gardamide, Paradisamide, Dimethyl anthranilate, Methyl anthranilate, n-Butyric acid, Capric acid, Caproic ac d, Caprylic acid, Phenylacetic acid, Caryophyllene oxide, Cedroxyde, Tobacarol The compounds of formula (1), formula (2), formula (3) or of formula (4) can accordingly be used for the production of compositions and, as will be evident from the foregoing compilation, a wide range of known odorants/fragrance, flavor and/or deodorizing/masking materials. In the production of such compositions, the known fragrance, flavor and/or deodorizing/masking materials referred to earlier can be used according to methods which are known to the perfumer such as, for example, according to W. A. Poucher, Perfumes, Cosmetics and Soaps 2, 7th Edition, Chapman and Hall, London 1974.

In an embodiment of the present invention, the claimed fragrance, flavor and/or deodorizing/masking composition comprises in addition to the acetals of formula (1) or of formula (2) or of formula (3) or of formula (4) at least one ester and/or one alcohol, preferably at least a mixture of ester and alcohol; the said ester and/or alcohol are preferably selected from the list defined herein above. In an embodiment of the present invention, the claimed odorant composition is characterized by a total content of the compound(s) of formula (1) or of formula (2) or of formula (3) or of formula (4) together with the ester(s) and/or alcohol(s) which is superior to 25 wt %, preferably superior to 50 wt %, for example superior to 75 wt %, or even superior to 90 wt %.

In another embodiment of the present invention, the claimed fragrance, flavor and/or deodorizing/masking composition comprises in addition to the acetals of formula (1) or of formula (2) or of formula (3) or of formula (4) their respective parent phenol of formula (5) or of formula (6) or of formula (7) or of formula (8). In an embodiment of the present invention the claimed odorant composition is characterized by a total content of the compound(s) of formula (1) or of formula (2) or of formula (3) or of formula (4) together with their respective parent phenol of formula (5) or of formula (6) or of formula (7) or of formula (8) which is superior to 5 wt %, e.g. superior to 25 wt %, preferably superior to 50 wt %, for example superior to 75 wt %, or even superior to 90 wt %.

In another embodiment of the present invention, the weight ratio between the acetals of formula (1) or of formula (2) or of formula (3) or of formula (4) and their respective parent phenol of formula (5) or of formula (6) or of formula (7) or of formula (8), in the claimed fragrance, flavor and/or deodorizing/masking composition, is comprised between 0.01/99.99 and 99.99/0.01, for example between 0.1/99.9 and 99.9/0.1, for example between 1/99 and 99/1, for example between 1/99 and 20/80. In another embodiment of the present invention, the weight ratio between the acetals of formula (1) or of formula (2) or of formula (3) or of formula (4) and their respective parent phenol of formula (5) or of formula (6) or of formula (7) or of formula (8), in the claimed fragrance, flavor and/or deodorizing/masking composition, is comprised between 80/20 and 99/1.

In another embodiment of the present invention, the claimed fragrance, flavor and/o deodorizing/masking composition in addition to the acetal of formula (1 formula (2) or of formula (3) or of formula (4) which are prepared by reacting the respective parent phenol of formula (5) or of formula (6) or of formula (7) or of formula (8) with ethoxyethene comprises, in addition, at least one of the side product(s) obtained during the said reaction step of the parent phenol and ethoxyethene.

Preparation

In a preferred embodiment according to the present invention, the compounds of formula (1), formula (2), formula (3) or of formula (4) can advantageously be prepared by reacting respectively 2-ethoxy-4-methylphenol (5); 3-ethoxy-4-(1-ethoxyethoxy)benzaldehyde (6); 2-ethoxy-4-(4-methyl-1,3-dioxolan-2-yl)phenol (7); and 2-ethoxy-4-(methoxymethyl)phenol (8) with ethoxyethene under acidic conditions.

Warning: Ethoxyethane can react violently with acids and care has to be taken when adding the acid catalyst to the reaction mixture. Inefficient cooling, or overdosing of hydrochloric acid can lead to a thermal overrun.

Example 1

Synthesis of 2-ethoxy-1-(1-ethoxyethoxy)-4-methylbenzene

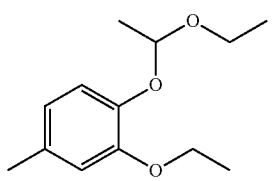

37% Hydrochloric acid (40 µl, 465 µmop was added to the mixture of 2-ethoxy-4-methylphenol (17.0 g, 112 mmol) and ethoxyethene (13.4 mL, 140 mmol) at 0° C. under dinitrogen while stirring. The mixture was stirred for 2 hr and was left overnight at 20° C. Subsequently, sodium carbonate (106 mg, 1 mmol) was added and volatiles were removed under reduced pressure. The crude product was distilled in vacuo using a Kugelrohr apparatus (100° C./1 mbar) to afford 2-ethoxy-1-(1-ethoxyethoxy)-4-methylbenzene (20.3 g, 81%) as a colorless liquid.

$^1$H NMR (500 MHz, DMSO-d6) δ 6.89 (d, J=8.0 Hz, 1H), 6.81 (d, J=1.8 Hz, 1H), 6.65 (dd, J=8.0, 1.3 Hz, 1H), 5.20 (q, J=5.2 Hz, 1H), 4.00 (q, J=7.0 Hz, 2H), 3.81-3.72 (m, 1H), 3.56-3.47 (m, 1H), 2.24 (s, 3H), 1.35 (d, J=5.2 Hz, 3H), 1.33 (t, J=7.0 Hz, 3H), 1.10 (t, J=7.1 Hz, 3H).

$^{13}$C NMR (125 MHz, DMSO-d6) δ=150.38, 143.9, 132.86, 121.34, 120.72, 115.05, 101.50, 64.07, 62.05, 21.14, 20.99, 15.56, 151.19

Example 2

Synthesis of 3-ethoxy-4-(1-ethoxyethoxy)benzaldehyde

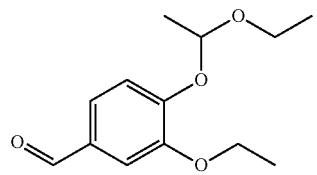 [SMILES: CCOc1cc(C=O)ccc1OC(C)OCC]

37% Hydrochloric acid (200 µL, 2.33 mmol) was added to the mixture of 3-ethoxy-4-hydroxybenzaldehyde (40.0 g, 241 mmol), ethoxyethene (13.4 mL, 301 mmol) and dichloromethane (50 mL) under dinitrogen while stirring. The mixture was stirred for 2 h and left for three days at 20° C. Subsequently, ethoxyethene (2.30 mL, 24 mmol) 37% hydrochloric acid (20 µL, 233 µmop) were added and the mixture was left overnight. Then sodium carbonate (950 mg, 9 mmol) was added and volatiles were removed under reduced pressure. The residue was distilled in vacuo using a Kugelrohr apparatus (146° C., 1 mbar) to afford 3-ethoxy-4-(1-ethoxyethoxy)benzaldehyde (47.0 g, 78%) as an off-white solid.

$^1$H NMR (500 MHz, DMSO-d6) δ 9.85 (s, 1H), 7.50 (dd, J=8.2, 1.9 Hz, 1H), 7.44 (d, J=1.9 Hz, 1H), 7.25 (d, J=8.2 Hz, 1H), 5.56 (q, J=5.2 Hz, 1H), 4.11 (q, J=7.0 Hz, 2H), 3.75-3.67 (m, 1H), 3.56-3.47 (m, 1H), 1.44 (d, J=5.2 Hz, 3H), 1.36 (t, J=7.0 Hz 3H), 1.11 (t, J=7.1 Hz, 3H).

$^{13}$C NMR (126 MHz, DMSO-d6) δ 191.5, 151.49, 149.54, 130.73, 124.95, 117.09, 11.93, 100.31, 63.93, 61.60, 20.21, 15.02, 14.54.

Example 3

Synthesis of 2-(3-ethoxy-4-(1-ethoxyethoxy)phenyl)-4-methyl-1,3-dioxolane

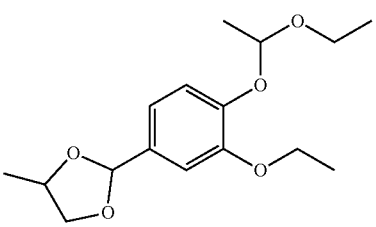 [SMILES: CCOc1cc(C2OCC(C)O2)ccc1OC(C)OCC]

37% Hydrochloric acid (56 µL, 651 µmol) was added to the mixture of 2-ethoxy-4-(4-methyl-1,3-dioxolan-2-yl)phenol (37.7 g 168 mmol) with ethoxyethene (21.3 mL, 223 mmol) under dinitrogen while stirring. The reaction mixture was stirred for 2 h and left for three days at 20° C. Subsequently, sodium carbonate (1.06 g, 10 mmol) was added and volatiles were removed under reduced pressure. The residue was distilled in vacuo using a Kugelrohr apparatus (165° C., 1 mbar) to afford 2-(3-ethoxy-4-(1-ethoxyethoxy)phenyl)-4-methyl-1,3-dioxolane (20.8 g, 42% ratio of diastereoisomers 44:56) as a colorless liquid.

$^1$H NMR (500 MHz, DMSO) δ 7.04-6.99 (m, 2H), 6.94 (dd, J=8.2, 1.9 Hz, 0.56H), 6.92 (dd, J=8.2, 1.9 Hz, 0.44H), 5.79 (s, 0.44H), 5.66 (s, 0.56H), 5.34-5.27 (m, 1H), 4.34-4.20 (m, 1.44H), 4.06-3.99 (m, 2.56H), 3.78-3.70 (m, 1H), 3.55-3.47 m, 1.56H), 3.45 (dd, J=7.9, 7.0 Hz, 0.44H), 1.37 (dd, J=5.2, 2.1 Hz, 3H), 1.33 (td, J=7.0, 2.1 Hz, 3H), 1.28 (d, J=6.1 Hz, 1.68H), 1.24 (d, J=6.1 Hz, 1.32H), 1.10 (td, J=7.0, 0.9 Hz, 3H).

$^{13}$C NMR (126 MHz, DMSO-d6) δ 149.63, 149.59, 146.42, 146.28, 133.26, 132.78, 119.12, 118.93, 112.02, 111.75, 102.90, 101.84, 100.77, 72.61, 71.70, 71.28, 70.59, 63.80, 61.51, 20.44, 18.53, 18.31, 15.07, 14.66.

Example 4

Synthesis of 2-ethoxy-1-(1-ethoxyethoxy)-4-methoxyethyl)benzene

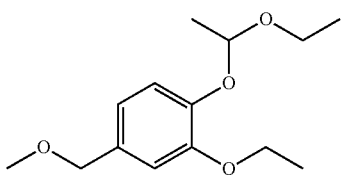

37% Hydrochloric acid (7 μL, 81 μmol) was added to the mixture of 2-ethoxy-4-(methoxymethyl)phenol (4.00 g, 22 mmol) and ethoxyethene (2.63 mL, 27.5 mmol) under dinitrogen while stirring. The reaction mixture was stirred for 2 h and left for three days at 20° C. Subsequently, sodium carbonate (106 mg, 1 mmol) was added and volatiles were removed under reduced pressure. The residue was distilled in vacuo using a Kugelrohr apparatus (260° C./6 mbar) to afford 2-ethoxy-1-(1-ethoxyethoxy)-4-(methoxymethyl) benzene (4.16 g, 74%) as a colorless liquid.

$^1$H NMR (500 MHz, DMSO-d6) δ 6.98 (d, J=8.1 Hz, 1H), 6.93 (d, J=1.9 Hz, 1H), 6.80 (dd, J=8.1, 1.9 Hz, 1H), 5.27 (q, J=5.2 Hz, 1H) 4.32 (s, 2H), 4.02 (q, J=7.0 Hz, 2H), 3.79-3.71 (m, 1H), 3.55-3.47 (m, 1H), 3.26 (s, 3H) 1.36 (d, J=5.2 Hz, 3H), 1.33 (t, J=7.0 Hz, 3H), 1.10 (t, J=7.1 Hz, 3H). $^{13}$C NMR (126 MHz, DMSO-d6) δ 149.79, 145.04, 133.12, 119.90, 119.55, 113.15, 100.83, 73.42, 63.68, 61.52, 57.30, 20.48, 15.08, 14.68.

Compositions Examples

In the following invention examples (B/C/D) were included in a musk accord fragrance for use in soap (A=blank).

| Raw Materials (parts by weight) | A Blank | B Comparative | C (1) Example | D Comparative |
| --- | --- | --- | --- | --- |
| Ambrettolide | 10 | 10 | 10 | 10 |
| Ambroxan | 1 | 1 | 1 | 1 |
| Iriswood (Keva) | 20 | 20 | 20 | 20 |
| Keflorol (Keva) | 15 | 15 | 15 | 15 |
| Musk 781 (Cervolide) | 50 | 50 | 50 | 50 |
| Tonalid | 250 | 250 | 250 | 250 |
| Ethyl vanillin | 0 | 0 | 0 | 5 |
| Ultravanil | 0 | 2 | 0 | 0 |
| 2-ethoxy-1-(1-ethoxyethoxy)-4-methylbenzene (1) | 0 | 0 | 2 | 0 |
| Dipropylene Glycol | 654 | 652 | 652 | 649 |
| TOTAL | 1000 | 1000 | 1000 | 1000 |

Comparative studies of different compounds where column A is the blank:

The introduction of 0.2% by weight of 2-ethoxy-1-ethoxyethoxy)-4-methylbenzene (compound (1)) provides the musk accord with a sweet and natural-animalic aspect as observed in musk Tincture. This effect develops further over time. (C). 2-ethoxy-1-(1-ethoxyethoxy)-4-methylbenzene (1) shows great photo-stability.

Compared to two other vanilla materials the following effects are observed: Introduction of 0.5% by weight of Ethyl vanillin gives a more sweet-musky effect, more "powdery" note; over time the soap discolors towards light brown (D). Introduction of 0.2% by weight of Ultravanil gives a strong phenolic effect turning the musk-note into a harsh-animalic smell. Over time a very slight discoloration of soap occurs (B).

In the following invention examples (B/C/D) were included in a spice accord fragrance for use in soap (A=blank).

| Raw Materials (parts by weight) | A Blank | B Comparative | C (1) Example | D Comparative |
| --- | --- | --- | --- | --- |
| Benzaldehyde | 12 | 12 | 12 | 12 |
| Cinnamic Aldehyde | 280 | 280 | 280 | 280 |
| Cinnamyl Nitrile | 200 | 200 | 200 | 200 |
| Clove bud oil | 315 | 315 | 315 | 315 |
| Ethyl Maltol | 5 | 5 | 5 | 5 |
| Litsea Cubeba Terpenes | 70 | 70 | 70 | 70 |
| Methyl octalactone | 3 | 3 | 3 | 3 |
| Nutmeg oil | 15 | 15 | 15 | 15 |
| Ethyl vanillin | 0 | 0 | 0 | 5 |
| Ultravanil | 0 | 2 | 0 | 0 |
| 2-ethoxy-1-(1-ethoxyethoxy)-4-methylbenzene (1) | 0 | 0 | 2 | 0 |
| Dipropylene Glycol | 100 | 98 | 98 | 95 |
| TOTAL | 1000 | 1000 | 1000 | 1000 |

Comparative studies of different compounds where column A is the blank:

The introduction of 0.2% by weight of 2-ethoxy-1-(1-ethoxyethoxy)-4-methylbenzene (compound (1)) provides the spice accord with an intense warm sweet aspect like natural vanilla beans. This effect develops further over time. (C). 2-ethoxy-1-(1-ethoxyethoxy)-4-methylbenzene shows great photo-stability.

Compared to 2 other vanilla materials the following effects are observed: Introduction of 0.5% by weight of Ethyl vanillin gives a synthetic, dry vanilla effect; over time the soap discolors towards light brown (D).

Introduction of 0.2% by weight of Ultravanil gives a strong phenolic effect; over time a very slight discoloration of soap occurs (B).

The invention claimed is:

1. A fragrance, flavor and/or deodorizing/masking composition comprising an acetal selected from compounds of formula (1), formula (2), formula (3) or of formula (4)

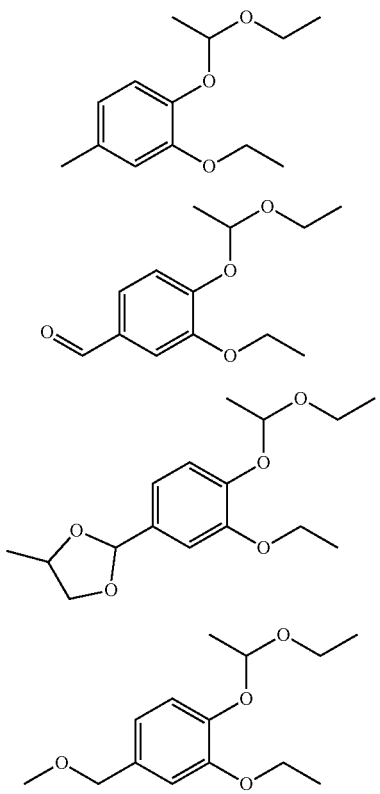

wherein compound (1) is 2-ethoxy-1-(1-ethoxyethoxy)-4-methylbenzene; compound (2) is 3-ethoxy-4-(1-ethoxyethoxy)benzaldehyde; compound (3) is 2-(3-ethoxy-4-(1-ethoxyethoxy)phenyl)-4-methyl-1,3-dioxolane; and compound (4) is 2-ethoxy-1-(1-ethoxyethoxy)-4-(methoxymethyl)benzene, and wherein the content of the acetal compound is comprised between 0.0001 and 95 wt %.

2. The fragrance, flavor and/or deodorizing/masking composition according to claim 1, wherein the composition filthier comprises at least one ester and/or one alcohol.

3. The fragrance, flavor and/or deodorizing/masking composition according to claim 2 wherein the total content of the compound(s) of formula (1) or of formula (2) or of formula (3) or of formula (4) together with the ester(s) and/or alcohol(s) is superior to 25 wt %.

4. The fragrance, flavor and/or deodorizing/masking composition according to claim 1 wherein the composition further comprises in addition to the acetals of formula (1) or of formula (2) or of formula (3) or of formula (4) their respective parent phenol of formula (5) or of formula (6) or of formula (7) or of formula (8)

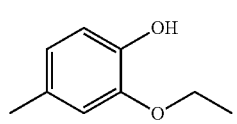

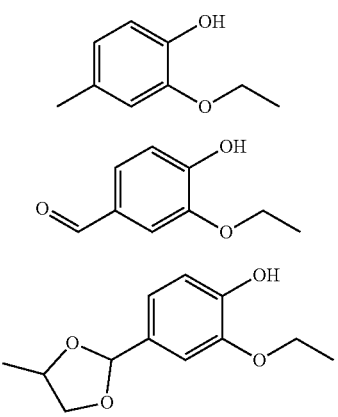

5. The fragrance, flavor and/or deodorizing/masking composition according to claim 4 wherein the total content of the compound(s) of formula (1) or of formula (2) or of formula (3) or of formula (4) together with their respective parent phenol of formula (5) or of formula (6) or of formula (7) or of formula (8) is superior to 5 wt %.

6. The fragrance, flavor and/or deodorizing/masking composition according to claim 4 wherein the weight ratio between the acetals of formula (1) or of formula. (2) or of formula (3) or of formula (4) and their respective parent phenol of formula (5) or of formula (6) or of formula (7) or of formula (8) is comprised between 0.01/99.99 and 99.99/0,01, for example between 0.1/99.9 and 99.9/0.1.

7. The fragrance, flavor and/or deodorizing/masking composition according to claim 4 wherein the weight ratio between the acetals of formula (1) or of formula (2) or of formula (3) or of formula (4) and their respective parent phenol of formula (5) or of formula (6) or of formula (7) or of formula (8) is comprised between 80/20 and 99/1.

8. The fragrance, flavor and/or deodorizing/masking composition according to claim 1 wherein the composition further comprises, in addition to the acetals of formula (1) or of formula (2) or of formula (3) or of formula (4), a reaction product of the reaction between the respective parent phenol of formula (5) or of formula (6) or of formula (7) or of formula (8)

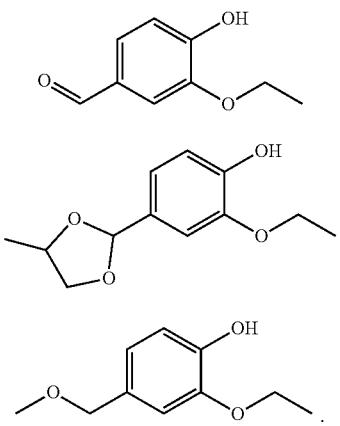

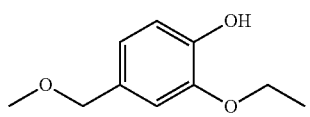

with ethoxyethene.

9. An acetal of formula (1), formula (3) or of formula (4) useful in the perfume, aroma and/or deodorizing/masking composition according to claim 1

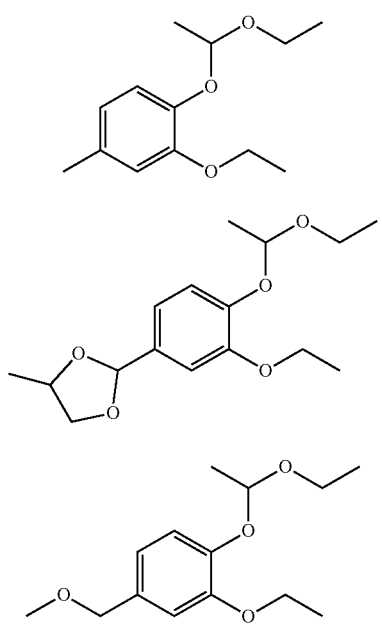

wherein compound (1) is 2-ethoxy-1-(1-ethoxyethoxy)-4-methylbenzene; compound (3) is 2-(3-ethoxy-4-(1-ethoxyethoxy)phenyl)-4-methyl-1,3-dioxolane; and compound (4) is 2-ethoxy-1-(1-ethoxyethoxy)-4-(methoxymethyl)benzene.

10. A perfumed or flavored product comprising the acetal according to claim 9.

11. A perfumed or flavored product comprising the fragrance, flavor and/or deodorizing/masking composition according to claim 1.

12. A fragrance, flavor and/or deodorizing/masking composition comprising an acetal selected from compounds of formula (1), formula (3) or of formula (4)

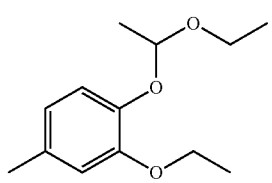

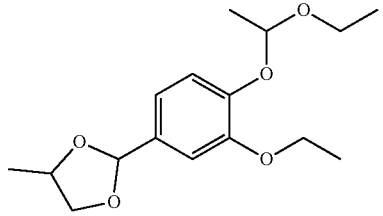

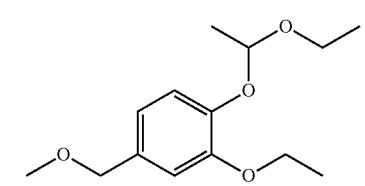 [SMILES: CCOc1cc(COC)ccc1OC(C)OCC]

wherein compound (1) is 2-ethoxy-1-(1-ethoxyethoxy)-4-methylbenzene; compound (3) is 2-(3-ethoxy-4-(1-ethoxyethoxy)phenyl)-4-methyl-1,3-dioxolane; and compound (4) is 2-ethoxy-1-(1-ethoxyethoxy)-4-(methoxymethyl)benzene.

13. The fragrance, flavor and/or deodorizing/masking composition according to claim 12, wherein the content of the acetal compound is comprised between 0.0001 and 95 wt %.

14. The fragrance, flavor and/or deodorizing/masking composition according to claim 13 wherein the content of the acetal compound is comprised between 0.1 and 10 wt. %.

15. A process for preparing acetal of formula (1), formula (3) or of formula (4)

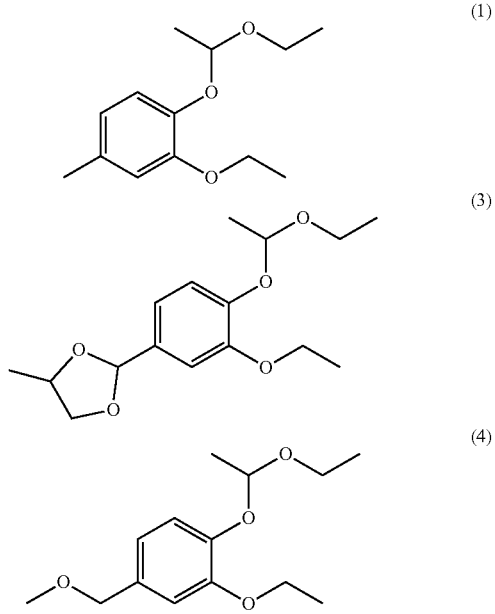

from compounds of formula (5), (7), (8) respectively

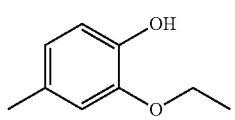

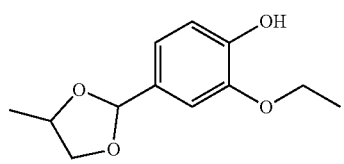 (7)
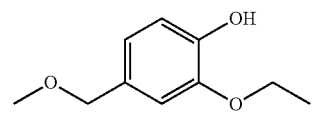 (8)
comprising subjecting said compounds of formula (5), (7), (8) to an acetalization synthesis step.
16. The process for preparing acetal according to claim 15 wherein the synthesis is performed by reacting the compounds of formula (5), (7), or (8) with ethoxyethene.
17. The process for preparing acetal according to claim 16 wherein the synthesis is performed under acidic conditions.
* * * * *